United States Patent
Affrime et al.

(10) Patent No.: US 7,405,223 B2
(45) Date of Patent: *Jul. 29, 2008

(54) TREATING ALLERGIC AND INFLAMMATORY CONDITIONS

(75) Inventors: Melton B. Affrime, Warren, NJ (US); Christopher R. Banfield, High Bridge, NJ (US); Samir K. Gupta, East Brunswick, NJ (US); Desmond Padhi, Thousand Oaks, CA (US)

(73) Assignee: Schering Corporation, Kenilworth, NJ (US)

(*) Notice: Subject to any disclaimer, the term of this patent is extended or adjusted under 35 U.S.C. 154(b) by 609 days.

This patent is subject to a terminal disclaimer.

(21) Appl. No.: 09/760,588

(22) Filed: Jan. 16, 2001

(65) Prior Publication Data

US 2002/0019409 A1  Feb. 14, 2002

Related U.S. Application Data

(60) Provisional application No. 60/179,910, filed on Feb. 3, 2000.

(51) Int. Cl.
*A61K 31/44* (2006.01)

(52) U.S. Cl. ...... 514/290; 514/960

(58) Field of Classification Search ........ 514/290, 514/318, 960
See application file for complete search history.

(56) References Cited

U.S. PATENT DOCUMENTS

| | | | | |
|---|---|---|---|---|
| 3,536,809 A | 10/1970 | Applezweig | | 424/28 |
| 3,598,123 A | 8/1971 | Zaffaroni | | 128/268 |
| 3,845,770 A | 11/1974 | Theeuwes et al. | | 128/260 |
| 3,916,899 A | 11/1975 | Theeuwes et al. | | 128/260 |
| 3,940,485 A | 2/1976 | Levinson et al. | | 424/250 |
| 4,008,796 A | 2/1977 | Aylon | | 198/460 |
| 4,282,233 A | 8/1981 | Vilani | | 424/267 |
| 4,371,516 A | 2/1983 | Gregory et al. | | 424/22 |
| 4,552,899 A | 11/1985 | Sunshine et al. | | 514/568 |
| 4,659,716 A | 4/1987 | Villani et al. | | |
| 4,731,447 A | 3/1988 | Schumacher et al. | | 546/93 |

(Continued)

FOREIGN PATENT DOCUMENTS

EP  0 264 259 A1  4/1988

(Continued)

OTHER PUBLICATIONS

Dipiro et al., Pharmacotherapy A Pathophysiologic Approach, New York, (1989), Chapter 65, pp. 945-953.*

(Continued)

*Primary Examiner*—Ardin Marschel
*Assistant Examiner*—Donna Jagoe
(74) *Attorney, Agent, or Firm*—Schering-Plough Patent Group

(57) ABSTRACT

A method of treating and/or preventing allergic and inflammatory conditions of the skin or upper and lower airway passages, e.g. seasonal allergic rhinitis, perennial allergic rhinitis, or chronic idopathic urticaria, in a human more 12 years old, by administering an amount of desloratadine, e.g. 2×2.5 mg or 5 mg/day for a time sufficient to produce a geometric mean steady state maximum plasma concentration of desloratadine in the range of about 2.90 ng/mL to about 4.54 ng/mL, or a arithmetic mean steady state maximum plasma concentration of desloratadine in the range of about 3.2 ng/mL to about 5.0 ng/mL is disclosed.

16 Claims, 3 Drawing Sheets

U.S. PATENT DOCUMENTS

| | | | | |
|---|---|---|---|---|
| 4,777,170 | A | 10/1988 | Heinrich | 514/226.2 |
| 4,783,465 | A | 11/1988 | Sunshine et al. | 514/255 |
| 4,804,666 | A | 2/1989 | Piwinski et al. | 514/278 |
| 4,863,931 | A | 9/1989 | Schumacher et al. | 514/290 |
| 4,906,647 | A | 3/1990 | Kouchiwa et al. | 514/356 |
| 4,990,535 | A | 2/1991 | Cho et al. | 514/556 |
| 5,019,591 | A | 5/1991 | Gardner et al. | 514/461 |
| 5,089,496 | A | 2/1992 | Piwinski et al. | 514/253 |
| 5,100,675 | A | 3/1992 | Cho et al. | 424/468 |
| 5,314,697 | A | 5/1994 | Kwan et al. | 424/480 |
| 5,407,941 | A | 4/1995 | Carceller et al. | 514/290 |
| 5,476,856 | A | 12/1995 | Carceller et al. | 514/290 |
| 5,502,080 | A * | 3/1996 | Hitzig | 514/654 |
| 5,595,997 | A * | 1/1997 | Aberg et al. | 514/290 |
| 5,698,558 | A * | 12/1997 | Gray | 514/255.04 |
| 5,731,319 | A | 3/1998 | Aberg et al. | 514/290 |
| 5,900,421 | A | 5/1999 | Handley et al. | 514/290 |
| 5,939,426 | A | 8/1999 | McCullough | 514/290 |
| 5,962,464 | A * | 10/1999 | Handley et al. | 514/290 |
| 6,051,585 | A | 4/2000 | Weinstein et al. | 514/335 |
| 6,054,463 | A | 4/2000 | Handley et al. | 514/290 |
| 6,100,274 | A | 8/2000 | Kou | 514/290 |
| 6,114,346 | A | 9/2000 | Harris et al. | 514/290 |
| 6,132,758 | A | 10/2000 | Munayyer et al. | 424/439 |
| 6,265,414 | B1 | 7/2001 | Harris et al. | 514/290 |
| 6,270,796 | B1 | 8/2001 | Weinstein | 424/457 |
| 6,423,721 | B1 | 7/2002 | Harris et al. | 514/290 |
| 6,432,972 | B2 * | 8/2002 | Salmun et al. | 514/291 |
| 6,506,767 | B1 | 1/2003 | Schumacher et al. | 514/290 |
| 6,514,520 | B2 | 2/2003 | Munayyer et al. | 424/439 |
| 6,521,254 | B2 | 2/2003 | Weinstein et al. | 424/468 |
| 6,599,913 | B1 | 7/2003 | Johnson et al. | 514/290 |
| 2003/0004179 | A1 | 1/2003 | Affrime et al. | |

FOREIGN PATENT DOCUMENTS

| | | |
|---|---|---|
| EP | 0 288640 A1 | 11/1988 |
| EP | 0 396404 A1 | 11/1990 |
| EP | 0 577 957 A1 | 1/1994 |
| EP | 0 396404 B1 | 2/1994 |
| WO | WO 85/03707 | 8/1985 |
| WO | WO 92/00293 | 1/1992 |
| WO | WO 92/11034 | 7/1992 |
| WO | WO 92/20377 | 11/1992 |
| WO | WO 96/16641 | 6/1996 |
| WO | WO 96/20708 | 7/1996 |
| WO | WO 98/34614 | 8/1998 |
| WO | WO 99/32125 | 7/1999 |
| WO | WO 00/02560 | 1/2000 |
| WO | WO 01/21161 A2 | 3/2001 |
| WO | WO 01/21162 A2 | 3/2001 |

OTHER PUBLICATIONS

Goodman & Gilman's, The Pharmacological Basis of Therapeutics, Ninth Edition, McGraw-Hill, New York, (1996), Chapter 50, p. 1192.*

W. Kreutner, et al., *Preclinical Efficacy and Antiallergic Profile of Desloratadine, a Selective and Nonsedating Histamine $H_1$-Receptor Antagonist* (Abstract 1118), J. Allergy Clin. Immunol., vol. 105, No. 1, part 2, pp. S382-S383 (Jan. 2000).

L. M. Salmun, et al., *Efficacy and Safety of Desloratadine in Seasonal Allergic Rhinitis* (Abstract 1123), J. Allergy Clin. Immunol., vol. 105, No. 1, part 2, pp. S384-S385 (Jan. 2000).

D. Padhi, et al., *Multiple-Dose Pharmacokinetics, Safety, and Tolerance of Desloratadine in Healthy Volunteers* (Abstract 1124), J. Allergy Clin. Immunol., vol. 105, No. 1, part 2, pp. S385 (Jan. 2000).

J. M. Herron, et al., *Dose-Proportionality, Linearity, and Pharmacokinetics of Desloratadine in Healthy Volunteers* (Abstract 1126), J. Allergy Clin. Immunol., vol. 105, No. 1, part 2, pp. S385 (Jan. 2000).

Andersen, et al., "Adverse drug interactions clinically important for the dermatologist", Arch Dermatol, Apr. 1995, vol. 131, pp. 468-473.

Babe, et al., "Histamine, Bradykinn, and their Antagonists" in The Pharmacological Basis of Therapeutics ($9^{th}$ edition), The McGraw-Hill Co. Inc., pp. 581-599 (1996).

Barnett, et al.,"Pharmacology of Non-Sedating H 1 Antihistamines", *New Perspectives in Histamine Research*, Birkhauser Verlag Basel, pp. 181-196 (1991).

Berge, et al., "Pharmaceutical Salts", J. of Pharm. Sciences, Jan. 1977, vol. 66, No. 1, pp. 1-19.

Berthon, et al., "In Vitro inhibition, by loratadine and descarboxyethoxyloratadine, of histamine release from human basophils, and of histamine release and intracellular calcium fluxes in rat basophilic leukemia cells (RBL-2H3)", Biochem. Pharm., 1994, vol. 47, No. 5, pp. 789-794.

Blaug, et al., "Interaction of dextroamphetamine sulfate with spray-dried lactose", J. of Pharm. Sciences, Nov. 1972, vol. 61, No. 11, pp. 1770-1775.

Brandes, et al., "Enhanced cancer growth in mice administered daily human-equivalent doses of some H1-antihistamines: predictive in vitro correlates", J. of the National Cancer Inst., May 18, 1994, vol. 86, No. 10, pp. 770-775.

Brandes, et al., "Stimulation of malignant growth in rodents by antidepressant drugs at clinically relevant doses", Cancer Research, Jul. 1, 1992, vol. 52, pp. 3796-3800.

Brion, et al., "Evaluation of the antimuscarinic activity of atropine, terfenadine and mequitazine in healthy volunteers", Br. J. Clin. Pharmac. 1988, vol. 25, pp. 27-32.

Carmeliet, "Voltage- and Time-Dependent Block of the Delayed K'0 Current in Cardiac Myocytes by Dofetilide", The J. of Pharm. And Experimental Therapeutics, 1992, vol. 262, No. 2, pp. 809-817.

Castello, et al., "Discoloration of tablets containing amines and lactose", J. of Pharm. Sciences, Feb. 1962,vol. 51, No. 2, pp. 106-108.

Cheung, et al., "Investigation of anti-motion sickness drugs in the squirrel monkey", J. Clin. Pharmacol, 1992, vol. No. 32, pp. 163-175.

Clissold, et al., "Loratadine: A preliminary review of its pharmacodynamic properties and therapeutic efficacy", Drugs, 1989,vol. 37, pp. 42-57.

Cooke, "Glycopyrrolate in bladder dysfunction", SA Medical Journal, Jan. 1, 1983, p. 3.

Craft, "Torsade de pointes after astemizole overdose", Br. Medical Journal, 1986,, vol. 292, p. 660.

Dorje, et al., "Antagonist Binding Profiles of Five Cloned Human Muscarinic Receptor Subtypes", The J. of Pharm. And Experimental Therapeutics, 1991, vol. 256, pp. 727-733.

Drug Facts and Comparisons, 1998 Ed., Facts and Comparisons, St. Louis, Missouri, p. 2832.

Ebert, "Soft elastic gelatin capsules: a unique dosage form", Pharmaceutical Technology, 1977, pp. 44-50.

Gengo, "Dilemma: Antihistamine selection: Use vs. Side effects", U.S. Pharmacist, Nov. 1990, pp. 59-92.

Hartauer, et al., A Comparison of Diffuse Reflectance FT-IR Spectroscopy and DSC in the Characterization of a Drug-Excipient Interaction, "Drug Development and industrial Pharmacy", 1991, vol. 17, No. 4, pp. 617-630.

Herzog, et al., "Urinary Incontinence: medical and Psychosocial Aspects", *Annual Review of Gerontology and Geriatrics*, 1989, vol. 9, pp. 74-119.

Hilbert, et al., "Pharmacokinetics and Dose Proportionality of Loratadine", J. Clin. Pharmacol. 1987, vol. 27, pp. 694-698.

Housley, et al., "Histamine and related substances influence neurotransmission of the semicircular canal", Hearing Research, May 1, 1988, vol. 35, pp. 87-97.

Jankowski, et al., "Effect of Terfenadine on Nnasal Provocation", Int. Arch. Allergy Immunolog., 1993, vol. 101, pp. 311-317.

Kaliner, "Nonsedating Antihistamines: Pharmacology, Clinical Efficacy and Adverse Effects", American Family Physician, Mar. 1992, vol. 45, No. 3, pp. 1337-1342.

Kleine-Tebbe, et al., "Inhibition of IgE- and non-IgE-mediated histamine release from human basophil leukocytes in vitro by a histamine H1-antagonist, desethoxycarbonyl-loratadine", J. Allergy Clin. Immunol., 1994, vol. 93, pp. 494-500.

Knowles, "Astemizole and Terfenadine-Induced Cardiovascular Effects", The Canadian J. of Hospital Pharmacy, Feb. 1992, vol. 45, No. 1, pp. 33 & 37.

Kohl, et al., "Lack of Effects of Astemizole on Vestibular Ocular Reflex, Motion Sickness, and Cognitive Performance in Man", Aviation, Space, and Environmental Medicine, Dec. 1987, pp. 1171-1174.

Kohl, et al., "New Pharmacologic Approaches to the Prevention of Space/Motion Sickness", J. Clin. Pharmacol., 1991, vol. 31, pp. 934-946.

Kohl., et al., "Control of Nausea and autonomic dysfunction with terfenadine, a peripherally acting antihistamine", Aviation, Space and Environmental Medicine, May 1991, pp. 392-396.

Kubo, et al., "Antimuscarinic Effects of Antihistamines: Quantitative Evaluation by Receptor-Binding Assay", Japan J. Pharmacol., 1987, vol. 43, pp. 277-282.

Lathers, et al., "Pharmacology in space: Part 2. Controlling motion sickness", TiPS, Jun. 1989, vol. 10, pp. 243-250.

Levin, et al., "Direct Measurement of the Anticholinergic Activity of a Series of Pharmacological Compounds on the Canine and Rabbit Urinary Bladder", The J. of Urology, Aug. 1982, vol. 128. pp. 396-398.

Lunde, "Antihistamines", *Side Effects of Drugs Annual 14*, Elsevier Science Publishers B.V., 1990, pp. 135-138.

Lunde, "Antihistamines", *Side Effects of Drugs Annual 12; A Worldwide Yearly Survey of New Data and Trends*, Elsevier Science Publishers B.V., 1998, pp. 142-143.

Massad, et al., "The Pharmacokinetics of Intravesical and Oral Oxybutynin Chloride", The J. of Urology, Aug. 1992, vol. 148, pp. 595-597.

McCue, "Safety of Antihistamines in the Treatment of Allergic Rhinitis in Elderly Patients", Arch. Fam. Med., Sep. 1996, vol. 5, pp. 464-468.

Miadonna, et al., "Inhibitory Effect of the H1 Antagonis Loratadine on Histamine Release from Human Basophils", Int. Arch. Allergy Immunol., 1994, vol. 105, pp. 12-17.

Mirakhur, et al., "Glycopyrrolate: Pharmacology and Clinical Use", Anaesthesia, 1983, vol. 38, pp. 1195-1203.

Mitchelson, "Pharmacological Agents Affecting Emesis: A Review (Part II)", Drugs, 1992, vol. 43, No. 4, pp. 443-463.

Muskat, et al., "The Use of Scopolamine in the Treatment of Detrusor Instability", The J. of Urology, 1996, vol. 156, pp. 1989-1990.

Nelemans, "Antiallergic and antitussive drugs", *Side Effects of Drugs Annual 12*, Elsevier Science Publishers B.V., 1988, pp. 144-147.

Nomeir, et al., "Influence of Food on the Oral Bioavailability of Loratadine and Pseudoephedrine from Extended-Release Tablets in Healthy Volunteers", J. Clin. Pharm, 1996, vol. 36, No. 10, pp. 923-930.

Parkinson, et al., "Evaluation of Loratadine as an Inducer of Liver Microsomal Cytochrome P450 in Rats and Mice", Biochemical Pharmacology, 1992, vol. 43, No. 10, pp. 2169-2180.

Peggs, et al., "Antihistamines: The Old and the New", American Family Physician, Aug. 1995, vol. 52, No. 2, pp. 593-600.

Petrin, "Bewegungskrankheit und ihre Therapie/ Eine Ubersicht (Motion Sickness and its Treatment)", Schweiz, Rundschau Med., 1974, (PRAXIS) 63, pp. 79-81.

Quercia, et al., "Focus on Loratadine: A new second-generation nonsedating H1-receptor antagonist", Hosp. Formul., Feb. 1993, vol. 28, pp. 137, 138, 141, 142, 144, 149, & 153.

Remington's Pharmaceutical Sciences. 18th Ed, Alfonso R. Gennaro, Mack Publishing Company, Easton, PA, 1990, pp. 1519-1520.

Remington's Pharmaceutical Sciences. 18th Ed, Alfonso R. Gennaro, Mack Publishing Company, Easton, PA, 1990, pp. 1527-1529.

Resnick, "Urinary incontinence", The Lancet, Jul. 8, 1995, vol. 346, pp. 94-99.

Roman, et al., "Loratadine-A Review of Recent Finding in Pharmacology Pharmacokinetics, Efficacy, and Safety, with a Look at its Use in Combination with Pseudoephedrine", Clin. Reviews in Allergy, 1993, vol. 11, pp. 89-110.

Simons, "H1-Receptor Antagonists Comparative Tolerability and Safety", Drug Safety, 1994, vol. 10, No. 5, pp. 350-380.

Sunahara, et al., "Pharmacological interventions for motion sickness: Cardiovascular Effects", Aviation, Space and Environmental Medicine, Sep. 1987, pp. A270-A276.

Temple, et al., "Loratadine, an Antihistamine, Blocks Antigen-and Ionophore-Induced Leukotriene Release from Human Lung In Vitro", Prostaglandins, Apr. 1988, 35(4):549-554.

Van Cauwenberge, "New Data on the Safety of Loratadine", Drug Invest., 1992, vol. 4, No. 4, pp. 283-291.

Van Peer, et al., "Ketoconazole Inhibits Loratadine Metabolism in Man", Beerse, Belgium, Abstract 1234, p. 34.

Wade, et al., Handbook of Pharmaceutical Excipients (2$^{nd}$ edition), American Pharmaceutical Association and Pharma Press, Royal Pharma. Society of G. Britain, 1994, pp. 257&259.

Wein, "Pharmacology of Incontinence", Urologic Clinics of North America, Aug. 1995, vol. 22, No. 3, pp. 557-577.

Wirth, et al., Mailland Reaction of Lactose and Fluoxeline Hydrochloride, a Secondary Amine, Journal of Pharmaceutical Sciences, Jan. 1998, vol. 87, No. 1, pp. 31-39.

Wood, "Antimotion Sickness and Antiemetic Drugs", Drugs, 1979, vol. 17, pp. 471-479.

Wood, et al., "Mechanisms of Antimotion Sickness Drugs", Aviation, Space, and Environmental Medicine, Sep. 1987, pp. A262-A265.

The United States Pharmacopeia, The United States Formulary, United States Pharmacopeial Convention, Inc., Rockville, MD. 1989, p. 1990.

Yarker, et al., "Oxybutynin,. A Review of its Pharmacodynamic and Pharmacokinetic Properties, and its Therapeutic Use in Detrusor Instability", Drugs and Aging, 1995, vol. 6, No. 3, pp. 243-262.

Zhong, et al., "HPLC-Determination of Loratadine and its active metabolite descarboethoxyloratadine in human plasma", Pharmazie, 1994, vol. 49(H. 10), pp. 736-739.

* cited by examiner

TREATING ALLERGIC AND INFLAMMATORY CONDITIONS

CROSS-REFERENCE TO RELATED APPLICATION

This application is a continuation-in-part application of, and claims priority under 35 U.S.C. §119 (e), to U.S. provisional application Ser. No. 60/179,910, filed Feb. 3, 2000, and now abandoned

BACKGROUND OF THE INVENTION

This invention relates to treating and/or preventing allergic and inflammatory conditions in a human by administering an amount of desloratadine for a time sufficient to produce a steady state mean plasma concentration of desloratadine to a human in need of such treating.

Loratadine is disclosed in U.S. Pat. No. 4,282,233 as a non-sedating antihistamine useful for treating allergic reactions in animals including humans. See also Claritin brand of Loratadine. Product Information Sheet, dated Jan 1999.Desloratadine is disclosed in U.S. Pat. No. 4,659,716 as a non-sedating antihistamine. The active metabolite of desloratadine, 3-hydroxydesloratadine, is disclosed in U.S. Pat. No. 4,804,666.

For clinical development of desloratadine, it was necessary to characterize the pharmacokinetics of desloratadine and its metabolites to determine the dose required to provide the appropriate concentrations at its sites of action. The desloratadine dose administered as well as the appropriate concentration attained at its sites of action are dependent upon the rate and extent of drug absorption, distribution; binding in tissues, biotransformation (metabolism) and excretion. The absorption, distribution, biotransformation and excretion of desloratadine all involve its transport across cell membranes.

Ideally, a drug should exhibit linear pharmacokinetics whereby the plasma concentrations of the drug plasma and the active drug metabolite(s), if any, increase in proportion to the drug dose. It is unpredictable which drugs will exhibit non-linear pharmacokinetics. This unpredictability may arise due to saturation of protein binding, hepatic metabolism or active renal transport of the drug and its active metabolite.

The molecular size, solubility at the site of absorption, degree of ionization and relative lipid solubility of the ionized and nonionized forms of a drug are important characteristics that affect the transport across cell membranes. These important characteristics are different for desloratadine (a secondary amine) and its active metabolite, 3-hydroxydesloratadine (a hydroxy-substituted secondary amine) and loratadine (a tertiary amine) so that transport across cell membranes and pharmacokinetics profiles may be different for each.

Drugs with non-linear pharmacoketics lack a proportional relationship between drug dose and drug plasma concentration which leads to burdensome physician and patient monitoring to achieve the targeted therapeutically effective plasma concentrations while avoiding significant periods of subtherapeutic or even toxic plasma levels.

There is a need for a clinically effective therapy for the use of desloratadine to treat or prevent such allergic and inflammatory conditions of the skin and airway passages in a human airway passages in a human.

SUMMARY OF THE INVENTION

The present invention provides a method of treating and/or preventing allergic and inflammatory conditions of the skin or airway passages in a human of 12 years and older in need of such treating and/or preventing which comprises administering an effective amount of desloratadine for a time sufficient to produce a geometric mean steady state maximum plasma concentration of desloratadine in the range of about 2.90 ng/mL to about 4.54 ng/mL, or an arithmetic mean steady state maximum plasma concentration of desloratadine in the range of about 3.2 ng/mL to about 5.0 ng/mL.

The present invention provides a method treating and/or preventing allergic and inflammatory conditions of the skin or airway passages in a human of 12 years and older in need of such treating and/or preventing which comprises administering an effective amount of desloratadine for a time sufficient to produce a geometric mean steady state maximum plasma concentration of 3-OH-desloratadine in the range of about 1.50 ng/mL to about 2.34 ng/mL, or an arithmetic mean steady state maximum plasma concentration of 3-OH-desloratadine in the range of about 1.60 ng/mL to about 2.50 ng/mL.

The present invention provides a method of treating and/or preventing seasonal or perennial allergic rhinitis in a human of 12 years and older which comprises administering an effective amount of desloratadine for a time sufficient to produce a geometric mean steady state maximum plasma concentration of desloratadine in the range of about 2.90 ng/mL to about 4.54 ng/mL, or an arithmetic mean steady state maximum plasma concentration of desloratadine in the range of about 3.2 ng/mL to about 5.0 ng/mL.

The present invention also provides a method of treating and/or preventing atopic dermatitis or urticaria in a human of 12 years and older in need of such which comprises administering an effective amount of desloratadine for a time sufficient to produce a geometric mean steady state maximum plasma concentration of desloratadine in the range of 2.90 ng/mL to about 4.54 ng/mL, or an arithmetic steady state mean maximum plasma concentration of desloratadine in the range of about 3.2 ng/mL to about 5.0 ng/mL.

The present invention also provides a method of treating and/or preventing allergic and inflammatory conditions of the skin or airway passages in a human of 12 years and older in need of such treating and/or preventing which comprises administering an effective amount of desloratadine for a time sufficient to produce a steady state geometric mean steady state maximum plasma concentration of desloratadine in the range of 2.90 ng/mL to about 4.54 ng/mL, or a steady state arithmetic mean maximum plasma concentration of desloratadine in the range of about 3.2 ng/mL to about 5.0 ng/mL.

The present invention provides a method of treating and/or preventing the nasal and non-nasal symptoms of seasonal and perennial allergic rhinitis and for treating chronic idiopathic urticaria in a human of 12 years and older in need of such treating and/or preventing which comprises administering to said human about 5.0 mg of desloratadine once a day for about 10 days to produce at an arithmetic mean time to maximum plasma concentration ($T_{max}$) of about 3 hours post dose, an arithmetic mean steady state maximum plasma concentration($C_{max}$) of desloratadine of about 4 ng/mL, and an area under the concentration-time curve of 56.9 ng.hr/mL of desloratadine.

The present invention provides a method of treating and/or preventing the nasal and non-nasal symptoms of seasonal and perennial allergic rhinitis and of treating chronic idiopathic urticaria in a human of 12 years and older in need of such treating and/or preventing which comprises administering an effective amount of desloratadine for a time sufficient to produce a steady state geometric mean plasma concentration of desloratadine in the range of about 2.90 ng/mL to about 4.54 ng/mL, or a arithmetic mean steady state maximum plasma concentration of desloratadine in the range of about 3.2 ng/mL to about 5.0 ng/mL.

The present invention provides a method of treating and/or preventing the nasal and non-nasal symptoms of seasonal and perennial allergic rhinitis and/or for treating chronic idiopathic urticaria in a human of 12 years and older in need of such treating and/or preventing which comprises administering to said human about 5.0 mg of desloratadine once a day for about 10 days to produce at an arithmetic mean time to maximum plasma concentration ($T_{max}$) of about 3 hours post dose, an arithmetic mean steady state maximum plasma concentration($C_{max}$) of desloratadine of about 4 ng/mL, and an area under the concentration-time curve of 56.9 ng.hr/mL of desloratadine.

DETAILED DESCRIPTION OF INVENTION

Figure 1:
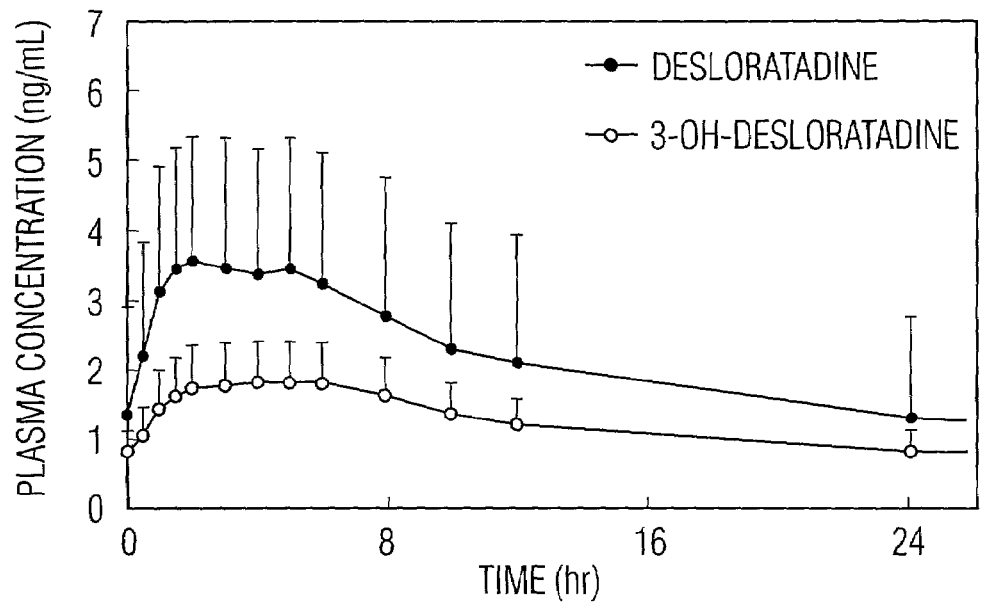
FIG. 1 is a linear: linear graphic display of the mean plasma concentrations of desloratadine ("DL") and 3-OH desloratadine ("3-OH DL") (ng/mL plasma) versus time(0-24 hours) on DAY 10, following multiple-dose oral administration of 5 mg desloratadine tablets to healthy adult subjects.

Desloratadine exhibits dose proportionality and linear, predictable pharmacokiinetics ($C_{max}$ and AUC) after oral administration of single doses of 5 mg to 20 mg. Following multiple daily oral dosing of 5 mg of desloratadine tablets, there are no clinically relevant differences in dosing females compared to males, or in dosing Blacks compared to Caucasians or in dosing geriatric patients (>65 years old) compared to younger patients (>12 years old and <65 years old). Thus, oral administration of desloratadine provides the patient and the physician with the confidence that a simple standard regimen (for example, 2.5 mg twice a day or 5 mg once a day) will produce the target serum concentrations of desloratadine and its active metabolite and the desired therapeutic effect without toxicity.

Desloratadine is metabolized in vivo into 3-OH-desloratadine. ("3-OH-DL") which is subsequently extensively converted into 3-OH desloratadine glucuronide. Desloratadine and 3-OH desloratadine are each non-sedating, long acting antihistamines with increased H1-receptor antagonist potency (compared to loratadine). Receptor binding data indicate that at a desloratadine concentration of 2-3 ng/mL (approximately 7 nanomolar), desloratadine shows significant interaction with the human histamine $H_1$ receptor. Desloratadine was rapidly absorbed from the gastrointestinal tract following oral administration of 5, 7.5, 10 or 20 mg desloratadine tablets. (Study No. 3) The $C_{max}$ for all doses was observed approximately 4 hours after administration, revealing no dose-related differences in absorption rate. $C_{max}$ and $AUC_{tf}$ [the area under the curve from time zero to the final concentration time point, (tf)] increased in a dose-proportional manner over a dose range of 5 to 20 mg. (See Table 4) Although the anticipated clinical dose is 5 mg/day, single doses of desloratadine as high as 20 mg/day, i.e., 4 times the recommended clinical dose of 5 mg/day, were safe and well tolerated. The $C_{max}$ and $AUC_{tf}$ for doses of 5 to 20 mg increased in a dose-proportional manner, showing that desloratadine has predictable linear pharmacokinetics. See Table 4.

Following oral administration of desloratadine dosed 5 mg once daily for 10 days to normal healthy subjects, the arithmetic mean time to steady state maximum plasma concentration ($T_{max}$) occurred at approximately 3 hours post dose on day 10 and a arithmetic mean steady state peak plasma concentratioins ($C_{max}$) was approximately 4.0 ng/mL and the area under the concentration-time (AUC) was 56.9 ng.hr/mL; the geometric mean time to steady state maximum plasma concentration ($T_{max}$) occurred at approximately 2.00 hours post dose on day 10 and the geometric mean steady state peak plasma concentrations ($C_{max}$) was approximately 3.63 ng/mL and the area under the concentrations-time curve (AUC) was 49.4 ng.hr/mL. See Table 2.

The phrase "allergic and inflammatory conditions of the skin or airway passages" is meant those allergic and inflammatory conditions and symptoms found on the skin and in the upper and lower airway passages from the nose to the lungs. Typical allergic and inflammatory conditions of the skin or upper and lower airway passages include seasonal and perennial allergic rhinitis, non-allergic rhinitis, asthma including allergic and non-allergic asthma, sinusitis, colds (in combination with a NSAID, e.g., aspirin ibuprofen or APAP) and/or a decongestant e.g. pseudoephedrine), dermatitis, especially allergic and atopic dermatitis, and urticaria and symptomatic dermographism as well as retinophathy, and small vessel diseases, associated with diabetes mellitus.

The term "a human of 12 years and older" as used herein means a male or female pediatric subject equal to, or greater than 12 years of age to less than 18years of age and adults of 18 years of age and older.

The amount of desloratadine effective for treating or preventing allergic and inflammatory conditions of the skin or airway passages will vary with the body weight and severity of the allergic and inflammatory condition of the patient. Typically, the amount of desloratadine effective for treating or preventing such allergic and inflammatory conditions in an adult human of 12 years of age and older is in the range of about 2.5 mg/day to about 45 mg/day, preferably about 2.5mg/day to about 20 mg/day, or about 5.0 mg/day to about 15 mg/day, or about 5.0mg/day to about 10 mg/day, more preferably about 5.0 mg/day to about 7.5mg/day, and most preferably about 5.0 mg/day in single or divided doses, e.g., 2.5 mg twice a day, i.e., 2×2.5 mg/day, or a single dose of 5.0 mg/day.

In the present invention, there is provided a safe and effective method of treating and/or preventing allergic and inflammatory conditions of the skin or upper and lower airway passages, e.g. seasonal allergic rhinitis, perenninal allergic rhinitis, or chronic idopathic urticaria, in a human more 12 years old, by administering an amount of desloratadine, e.g., 2×2.5 mg or 5 mg/day for a time sufficient to produce a geometric mean steady state maximum plasma concentration of desloratadine in the range of about 2.90 ng/mL to about 4.54ng/mL, or a arithmetic mean steady state maximum plasma concentration of desloratadine in the range of about 3.2 ng/mL to about 5.0 ng/mL.

Desloratadine is a non-sedating long acting histamine antagonist with potent selective peripheral H1-receptor antagonist activity. Following oral administration, loratadine is rapidly metabolized to descarboethoxyloratadine or desloratadine, a pharmacologically active metabolite. In vitro and in vivo animal pharmacology studies have been conducted to assess various pharmacodynamic effects of desloratadine and loratadine. In assessing antihistamine activity in mice (comparison of $ED_{50}$ value), desloratadine was relatively free of producing alterations in behavior alterations in behavior, neurologic or autonomic function. The potential for desloratadine or loratadine to occupy brain H1-receptors was assessed in guinea pigs following i.p. administration and results suggest poor access to central histamine receptors for desloratadine or loratadine.

The in vivo studies also suggest that an inhibitory effect of desloratadine on allergic bronchospasm and cough can also be expected.

The clinical efficacy and safety of desloratadine has been documented in over 3,200 seasonal allergic rhinitis patients in 4 double-blinded, randomized clinical trials. The results of these clinical studies demonstrated the efficacy of desloratadine in the treatment of adult and adolescent patients with seasonal rhinitis.

Efficacy endpoints in all the studies were Total Symptom Score, Total Nasal Symptom Score, Total Non-nasal Symptom Score, and Health Quality of Life (HQOL) analysis in efficacy trials. Desloratadine (5 mg once daily) significantly reduced the total symptom scores (the sum of individual scores for rhinorrhea, sneezing, congestion/stuffiness, nasal itching, itchy/burning eyes, tearing, ocular redness, and itchy ears/palate). Desloratadine (5 mg) was significantly ($p<0.01$) more effective than placebo in reducing nasal symptoms. An important efficacy endpoint analyzed in the desloratadine studies is the AM NOW total symptom score. This parameter measures the total symptom relief by the patient after 24 hours before taking the next day dose. Statistically significant ($p<0.05$) reductions were maintained for the full 24 hour dosing interval over the entire 5 mg to 20 mg dosage range.

There were no significant differences in the effectiveness of desloratadine (over the entire 5 mg to 20 mg dosage range) across subgroups of patients defined by gender, age, or race. Desloratadine is particularly useful for the treatment and prevention of the nasal (stuffiness/congestion, rhinorrhea, nasal itching, sneezing) and non-nasal (itchy/burning eyes, tearing/watery eyes, redness of the eyes, itching of the ears/palate) symptoms of seasonal and perennial allergic rhinitis, including nasal congestion, in patients in need of such treating and/or preventing.

Desloratadine is also useful for the treatment of chronic idiopathic urticaria.

Oral administration of desloratadine significantly reduced the severity of pruritis, number of hives and size of largest hive, total symptom score, interference with sleep and the interference with daily activities. Symptoms of chronic idiopathic urticaria were reduced following the first dose of a 5 mg desloratadine tablet and maintained for a full 24 hour dosing interval.

Desloratadine is contraindicated in patients who are hypersensitive to this medication or to any of its ingredients.

CLINICAL STUDY DESIGN

Study No. 1

Study Objective

The pharmacokinetic objective of this study was to characterize the pharmacokinetic profile of desloratadine and 3-OH desloratadine following multiple-dose oral administration of 5 mg of desloratadine to a population representative of that studied in the clinical efficacy and safety seasonal allergic rhinitis phase III program.

INVESTIGATIONAL PLAN

Overall Study Design and Plan: Description

A total of 113 of 114 healthy adult subjects (57 males and 56 females) were enrolled and 112 successfully completed this open-label, multiple-dose study.

Subjects were screened within 3 weeks of dosing, and those who met the entry criteria were confined to the study center within 24 hours prior to treatment (Day-1). Each subject received a 5 mg desloratadine tablet orally (once daily at 8 AM for 10 days).

Each dose was administered with 180 mL (6 fl oz) of non-carbonated room temperature water. The tablet was swallowed whole, not chewed or crushed. After dosing, the oral cavity was inspected to assure that the subject had swallowed the tablet.

All subjects were confined to the study site until the 120-hour study related procedures were obtained. No strenuous physical activity was permitted, and the subjects were not allowed visitors while they were confined to the study site.

Vital signs and ECGs were performed, and blood samples were collected at pre-specified times for safety and pharmacokinetic evaluations. Subjects were continually observed and questions throughout the study for possible occurrence of adverse events. Subjects were also instructed to report any unusual experiences or discomfort.

Study Population/Inclusion Criteria/Exclusion Criteria
Inclusion Criteria:
Subjects who were Caucasian or African-American with both parents being Caucasian or African-American, respectively.
Subjects were healthy adult males or females between the ages of 18 and 70 years inclusive, and had a Body Mass Index (BMI) between 19-27. [BMI=weight (kg)/height $(m^2)$]
Clinical laboratory tests (CBC, blood chemistries, urinalysis) were within normal limits or clinically acceptable to the Investigator/Sponsor.
Drug screen for drugs with a high potential for abuse were negative at screening and on admission to the study site.
Subjects were free of any clinically significant disease that required a physician's care and/or may have interfered with study evaluations, procedures or participation.
Subject gave written informed consent (prior to any study-related procedures being performed) and were willing to adhere to restrictions and examination schedules.
Subjects had a normal or clinically acceptable physical examination and ECG.

Exclusion Criteria:

Subjects who had a history of any local or systemic infectious disease within four weeks prior to initial treatment administration.

Subjects who did not comply with the requirement that he or she should not have used any prescription drugs including loratadine (or over-the-counter drugs (except acetaminophen, also called paracetamol) within 72 hours) within 14 days prior to the study nor alcohol or xanthine-containing substances with 72 hours prior to study drug administration.

Subjects who had taken astemizole (or other long half-life drugs) within 3 months prior to drug administration (Day 1).

Subjects who had received any drugs known to induce hepatic cytochrome P450 enzymes within 30 days prior to the start of the study (e.g., rifampin)

Subject who had received any drugs known to inhibit hepatic cytochrome P450 enzymes within 30 days prior to start of the study (e.g., ketoconazole).

Subjects who had taken any investigational drug within 30 days prior to the start of the study. (Day 1)

Subjects who were, or were known to be former, narcotic addicts or alcoholics.

Subjects who were positive for hepatitis B surface antigen or hepatitis C antibody.

Subjects who were positive for HIV antibodies.

Subjects who had a clinically significant history of food or drug allergy.

Subjects who had a known allergy or intolerance to antihistamines including loratadine.

Females who had a positive serum/urine pregnancy test at screening or on admission to the study site.

Females who were lactating or unwilling to use/practice an adequate barrier method of contraception.

Subjects who had previously received desloratadine or Claritin (brand of loratadine) within 30 days of drug administration (Day-1).

Study Treatments

Subjects were confined to the study site at least 12 hours prior to treatment (Day-1) until the 120-hour blood sample, vital signs and laboratory tests were obtained on Day 15. In the mornings of Days 1 through 10, each subject received a single 5 mg tablet of desloratadine. Each dose was administered with 180 mL (6 fl. oz.) of non-carbonated room temperature water. The tablet was swallowed whole, not chewed or crushed. After dosing, the oral cavity was inspected to assure that the subject had swallowed the tablet. An overnight fast was only required prior to dosing on Day 10. The fast continued until the 4-hour blood samples had been collected. No food or fluid (except water) was permitted during the fasting period. Subjects were to remain upright/ambulatory for 4 hours after dosing.

The desloratadine tablets were manufactured in accordance with Example 11 of U.S. Pat. No. 6,100,274 and packaged by Schering Corporation, Kenilworth, N.J., U.S.A and supplied to the Investigator.

Method of Treatment Assignment

Upon confinement at the research center and after fulfilling all the study entry requirements, subjects were sequentially allocated subject numbers Subjects who withdrew or were removed from the study were to be replaced at the discretion of the Sponsor.

Prior and Concomitant Therapy

No other medications (investigational, prescription or OTC) except acetaminophen (within 72 hrs) were taken by the subjects within 14 days of treatment initiation or during the course of the study without prior approval from the Principal Investigator or Sponsor unless it was a medical emergency. The use of any medications, including analgesics and over-the-counter medications that may have been used to treat adverse events, were to be recorded on the appropriate page of the case record form.

Pharmacokinetics

Blood samples were collected for determination of the plasma pharmacokinetic profile of desloratadine and 3-OH desloratadine. Five milliliters (5 mL) of blood were collected just prior to drug administration (0 hour) and at 0.5, 1, 1.5, 2, 3, 4, 5, 6, 8, 10,12, 24, 48, 72, 96 and 120 hours after dosing on Day 10. Additional blood samples were obtained immediately prior to dosing (0-hour) on Days 1, 7, 8 and 9 to determine if a steady-state had been obtained. All blood samples were collected into heparin-containing tubes at the specified times. The blood samples were centrifuged within 30 minutes after collection for 15 minutes at approximately 4° C. and at approximately 1500 g. The plasma was separated and transferred into two separate appropriately labeled tubes, frozen to at least −20° C. and maintained in the frozen state until assayed for desloratadine, and 3-OH desloratadine content.

The plasma concentration data for desloratadine following administration of 5 mg of desloratadine were used to estimate the following pharmacokinetic parameters:

| | |
|---|---|
| $C_{max}$ - | maximum observed plasma concentration |
| $T_{max}$ - | time of observed maximum plasma concentration |
| $AUC_{(tf)}$ - | area under the plasma concentration vs time curve from time zero to the final measurable sampling time (tf) |
| AUC(0-24) - | area under the plasma concentration vs time curve from time zero to 24 hours |
| $C_{min}$ - | minimum observed plasma concentration pre-dose levels on Days 7, 8, 9 and 10 |

The pharmacokinetic variables of major interest were the plasma AUC(0-24) and $C_{max}$. Plasma desloratadine and 3-OH desloratadine concentrations were determined using a validated liquid chromatography with tandem mass spectrometric detection ("LC/MS/MS") method with the lower limits of quantitation ("LOQ") of 0.025 ng/mL and linear ranges of 0.025 to 10 ng/mL in human plasma for each analyte. Individual plasma concentration-time data were used to determine the pharmacokinetic parameters using model-independent methods. The maximum plasma concentration ($C_{max}$) and time of maximum plasma concentration ($T_{max}$) were the observed values. The terminal phase rate constant (K) was calculated as the negative of the slope of the log-linear terminal portion of the plasma concentration-time curve using linear regression. The terminal phase half-life (t½) was calculated as 0.693/K.

The area under the plasma concentration-time curve (AUC) from time zero to the time of the final quantifiable sample [AUC(tf)] and the AUC from time zero to 24 hrs [AUC(0-24 hrs)] were calculated using the trapezoidal method.

Statistical Analyses

Summary statistics for the concentration data at each sampling time and the derived pharmacokinetic parameters were calculated for each analyte (desloratadine, and 3-OH desloratadine).

Safety Measurements Assessed

For safety evaluation, physical examinations, vital signs, electrocardio-grams and clinical laboratory tests were conducted at screening and at the conclusion of the study. In addition, vital signs were monitored prior to treatment administration and daily during both treatment periods. The assessment, severity and relationship to treatment of adverse events were evaluated.

SUMMARY CONCLUSIONS

RESULTS: The Study was Conducted as Planned.

Mean minimum ($C_{min}$) or trough plasma desloratadine concentrations on Days 7, 8, 9 and 10 are presented in Table 1. The mean plasma desloratadine and 3-OH desloratadine trough concentrations of Days 7, 8, 9 and 10, were within 10% of one another suggesting that steady-state was attained by Day 7 following administration of 5 mg of desloratadine.

TABLE 1

Mean Minimum Plasma Concentration (Cmin) of DL and 3-OH DL Following Multiple Oral Dosing of DL 5 mg to Healthy Subjects on Days 7, 8, 9 and 10

| Compound | | Cmin(ng/mL) | | | |
|---|---|---|---|---|---|
| | | Day 7 | Day 8 | Day 9 | Day 10 |
| | | All Subjects | | | |
| DL | Arithmetic Mean (% CV)[1] | 1.26(96) | 1.31(104) | 1.33(107) | 1.38(114) |
| | Geometric Mean | 1.02 | 1.04 | 1.05 | 1.07 |
| 3-OH-DL | Arithmetic Mean (% CV) | 0.792(35) | 0.811(35) | 0.808(35) | 0.845(36) |
| | Geometric Mean | 0.738 | 0.755 | 0.756 | 0.786 |

[1]% CV were not calculated for non-arithmetic means

Figure 2:
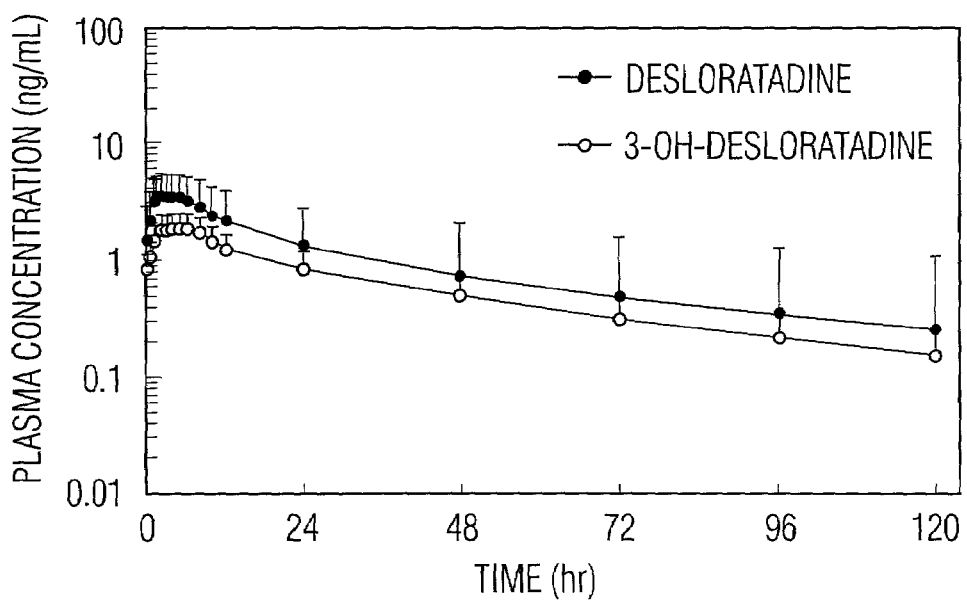
FIG. 2 is a log: linear graphic display of the mean plasma concentrations of desloratadine ("DL") and 3-OH desloratadine ("3-OH DL") (ng/mL plasma) versus time (0-24 hours) on DAY 10, following multiple-dose oral administration of 5 mg desloratadine tablets to healthy adult subjects.

Desloratadine was rapidly absorbed following oral administration of the 5 mg desloratadine tablets. Maximum geometric mean steady state plasma desloratadine concentrations ($C_{max}$) were achieved at about 2 hr post-dose (geometric mean or median $T_{max}$ value) on Day 10, following multiple-dose oral administration of 5 mg desloratadine tablets to healthy adult subjects. The median $T_{max}$ value for 3-OH desloratadine is 5 hrs. The arithmetic and harmonic mean t½ values of DL were 26.8 and 24.2 hours, respectively, following desloratadine administration (See Table 2. See also FIGS. 1 and 2.)

TABLE 2

Mean Pharmacokinetic Parameters of Desloratadine and 3-OH Desloratadine Following Multiple Oral Dosing of DL 5 mg[1] to Healthy Subjects on Day 10

| | | Pharmacokinetic Parameters | | | |
|---|---|---|---|---|---|
| | | Cmax (ng/mL) | Tmax (hr) | AUC(0–24 hr) (ng-hr/mL) | t½ (hr) |
| DL | Arithmetic Mean | 3.98 | 3.17 | 56.9 | 26.8 |
| | % CV | 52 | 56 | 73 | 50 |
| | Geometric Mean | 3.63 | 2.00[a] | 49.4 | 24.2[c] |

TABLE 2-continued

Mean Pharmacokinetic Parameters of Desloratadine and 3-OH Desloratadine Following Multiple Oral Dosing of DL 5 mg[1] to Healthy Subjects on Day 10

| | | Pharmacokinetic Parameters | | | |
|---|---|---|---|---|---|
| | | Cmax (ng/mL) | Tmax (hr) | AUC(0–24 hr) (ng-hr/mL) | t½ (hr) |
| 3-OH DL | Arithmetic Mean | 1.99 | 4.76 | 32.3 | 36.0 |
| | % CV | 31 | 40 | 31 | 33 |
| | Geometric Mean | 1.87 | 5.00 | 30.4 | 34.0[c] |

[1]5 mg DL tablet made in accordance with Example 11 of U.S. Pat. No. 6,100,274
[a]Median(geometric mean) Tmax
[b]Value not calculated.
[c]Harmonic mean.
% CV were not calculated for non-arithmetic means.

Conclusions:

Vital Signs, Physical Findings and Other Observations Related to Safety

Blood pressure, pulse rate, electrocardiograms and oral body temperature evaluations showed no consistent changes of clinical relevance and remained within the range observed for healthy adult subjects.

Discussion and Overall Conclusions

This study was conducted to characterize the pharmacokinetic profile of desloratadine and 3-OH desloratadine following multiple-dose administration of 5 mg desloratadine tablet in a population representative of that studied in the clinical seasonal allergic rhinitis program. At this dose, geometric mean maximum steady state concentrations are attained at 2 hours (median $T_{max}$) after dosing and desloratadine was slowly eliminated with a mean half-life (arithmetic mean) of 26.8 hours; the geometric mean or median half-life was 24.2 hours. Evaluation of the relationship of age and the disposition of desloratadine showed that there appeared to be a 30% increase in the t½ in elderly subjects ≧65 years old compared with younger subjects. These age-related differences are not clinically relevant and no dosage modification in this elderly age group is required.

Conclusions

Five mg desloratadine administered once daily for 10 days was safe and well tolerated.

Following multiple dose oral administration of 5 mg desloratadine, steady state arithmetic mean $C_{max}$ and AUC values for all subjects were 3.98 ng/mL and 56.9 ng-hr/mL, respectively, for desloratadine.

Desloratadine was absorbed with a geometric mean or median $T_{max}$ of 2 hr, and a arithmetic mean or mean $T_{max}$ of about 3 hr.

Desloratadine was eliminated with an arithmetic mean t½ of 26.8 hours.

No dosage modification is warranted in elderly subjects.

STUDY NO. 2

Pharmacokinetic Objective

The pharmacokinetic objective of this study was to characterize the pharmacokinetic profile of desloratadine in adult subjects differing in race and sex following multiple-dose oral administration of 7.5 mg desloratadine tablets to such subjects.

This open-label, parallel group, multiple-dose study of desloratadine was conducted in 12 black men (19-38 years old), 12 white men (19-39 years old), 12 black women (24-41 years old) and 12 white women (28-45 years old). Each adult subject received a single oral dose of desloratadine 7.5 mg, followed 3 days later by once-daily dosing for 14 days. Plasma concentrations of desloratadine and 3 hydroxydesloratadine ("3-OH-DL") were determined by liquid chromatography/mass spectometry (LOQ=0.025 ng/mL). Steady state was characterized by the following mean % coefficient of variation (%CV)) pharmacokinetic parameters for desloratadine and 3-OH-DL after 14 days of dosing listed in Table 3.

TABLE 3

Mean (% CV) Desloratadine Pharmacokinetic Parameters on Day 14 Following Once Daily Oral Administration of 7.5 mg Desloratadine for 14 Days to Healthy Adult Subjects Differing in Race and Gender.

| Parameter for | White | | Black | |
|---|---|---|---|---|
| DL | Men | Women | Men | Women |
| $AUC_{[0-24]}$ (ng.hr/mL) | 98.1(136) | 74.5(44) | 135(122) | 107(73) |
| $C_{max}$ (ng/mL) | 6.05(99) | 5.46(36) | 7.52(103) | 6.73(48) |
| $t_{1/2}$ (hr) | 36.0(51) | 29.9(14) | 42.0(53) | 35.4(42) |

Discussion

Statistical evaluations of the log-transformed AUC and $C_{max}$ values show that female subjects had 3% and 10% higher desloratadine values, respectively, compared with male subjects. The AUC and $C_{max}$ values for desloratadine were 32% and 18% higher in Black subjects compared with Caucasian subjects. These differences were not clinically relevant and, therefore, no dosage adjustment is required for race or sex. Accumulation [ratio of multiple dose $AUC_{[0-24)}$: single dose $AUC_{[0-24)}$] of desloratadine was consistent with its $t_{1/2}$ and dosing frequency. Headache was the most frequently reported adverse event and occurred exclusively in women of both races.

Conclusions

Desloratadine (7.5 mg) orally admnistered once daily for 14 days was safe and well tolerated Differences in AUC and $C_{max}$ values were not clinically significant in subjects differing in race and gender.

No dosage adjustment in desloratadine is needed due to differences in race or gender.

The 5.0 mg once daily or 2.5 mg twice daily of desloratadine is the preferred dose

STUDY NO. 3

Study Objective

The relationship between dose and pharmacokinetic behavior is important in drug development because of the potential clinical implications. Therefore, this open-label, four-way crossover study in 20 healthy subjects was designed to evaluate the does proportionality (linearity) of single-doses of desloratadine. A single dose of desloratadine (5 mg, 7.5 mg, 10 mg and 20 mg) was administered under fasted conditions in each of four treatment periods.

Study Objectives

The objective of this study was to evaluate the dose proportionality, linearity and pharmacokinetic profile of desloratadine after single oral doses of desloratadine at four dose levels (5 mg, 7.5 mg, 10 mg and 20 mg).

Investigational Plan

Overall Study Design and Plan: Description

A total of 20 healthy subjects were enrolled and successfully completed this randomized, open-label, single-dose, four-way crossover study.

Subjects were screened within 3 weeks of dosing, and those who met the entry criteria were confined to the study center within 12 hours prior to each treatment (Day-1). Upon confinement, subjects had safety laboratory tests and electrocardiograms repeated. The following morning, after fasting for a minimum of 10 hours, subjects received one of the following four treatments based on his/her subject number and the study period:

| Treatment A: | One desloratadine 5 mg tablet |
|---|---|
| Treatment B: | One desloratadine 7.5 mg tablet |
| Treatment C: | One desloratadine 10 mg tablet |
| Treatment D: | Two desloratadine 10 mg tablets (20 mg total) |

All subjects were confined to the study site until the 168-hour study related procedures were obtained. No strenuous physical activity was permitted, and the subjects were not allowed visitors while they were confined to the study site. A physician was present for all drug administrations and remained on the study site for at least four hours postdose. A washout period of at least 14 days separated each of the dose administrations in each treatment period in the study.

Vital signs and ECGs were performed, and blood samples were collected at pre-specified times for safety and pharmacokinetic evaluations. Subjects were continually observed and questioned throughout the study for possible occurrence of adverse events. Subjects were also instructed to report to site personnel any unusual experiences or discomfort. Overall Study Design: Discussion This study was conducted to determine the dose proportionality, linearity, and pharmacokinetic profile (AUC and Cmax) of desloratadine, administered as a single-dose at four different dosage strengths in an open-label, randomized, four-way crossover design. The Inclusion Criteria and Exclusion Criteria of Study No. 1 were used.

Study Treatments

Subjects were confined to the study site at least 12 hours prior to each treatment administration. On the morning of Day 1, following a 10-hour overnight fast, each subject received one of the following treatments based on his/her subject number and the study period. The order of treatment administration was determined according to a computer-generated random code supplied to the Investigator by the Sponsor.

| Treatment A: | One desloratadine 5.0 mg tablet administered after a 10-hour fast. |
|---|---|
| Treatment B: | One desloratadine 7.5 mg tablet administered after a 10-hour fast. |
| Treatment C: | One desloratadine 10 mg tablet administered after a 10-hour fast |

-continued

| Treatment D: | Two desloratadine 10 mg tablets (20 mg total) tablet administered after a 10-hour fast. |
|---|---|

Each dose was administered with 180 mL (6 fl oz) of non-carbonated room temperature water. The tablet was swallowed whole, not chewed or crushed. After dosing, the oral cavity was inspected to assure that the subject had swallowed the tablet(s). Subjects continued fasting until the 4-hour study procedures were completed, at which time lunch was served. Water was permitted throughout the fasting period. The subjects remained awake and seated upright/ambulatory for 4 hours postdose. Subjects were under medical supervision throughout their confinement at the study site. Each treatment administration was separated by at least a 14 day washout period. The desloratadine tablets were prepared in accordance with Example 11 of U.S. Pat. No. 6,100,274, packaged and supplied to the Investigator by Schering-Plough Research Institute, Kenilworth, N.J., USA of Example 11 of U.S. Pat. No. 6,100,274.

The arithmetic (%CV) and geometric and harmonic mean pharmacokinetic parameters of desloratadine are summarized in Table 4:

TABLE 4

Arithmetic(% CV) and Geometric Mean Pharmacokinetic Parameters of Desloratadine

| Parameter[c] | 5 mg[a,b] | | 7.5 mg[a,b] | | 10 mg[a,b] | | 20 mg[a,b] | |
|---|---|---|---|---|---|---|---|---|
| | Arithmetic Mean(% CV) | Geometric Mean | Arithmetic Mean(% CV) | Geometric Mean | Arithmetic Mean(% CV) | Geometric Mean | Arithmetic Mean(% CV) | Geometric Mean |
| Cmax | 2.18(33 ) | 2.07 | 3.03(31) | 2.88 | 3.80(29) | 3.66 | 8.08(26) | 7.83 |
| DN[d] Cmax | 2.18 | 2.07 | 2.02 | 1.92 | 1.90 | 1.83 | 2.02 | 1.96 |
| AUC(tf) | 78.0(127) | 53.3 | 104(93) | 80.4 | 126(98) | 95.1 | 290(92) | 222 |
| DN[d-] AUC(tf) | 78.0 | 53.3 | 69.2 | 53.6 | 63.0 | 47.6 | 72.4 | 55.4 |

[a]Dose
[b]n = 20
[c]Unit: Cmax-ng/mL; AUC(tf)-ng. hr/mL.
[d]Dose-normalized to 5 mg.

The peak plasma desloratadine concentrations ($C_{max}$) were observed at about 4 hours after dosing, over the dose range of 5 mg to 20 mg suggesting no dose-related changes in the absorption rate of desloratadine. The intersubject variability of Cmax expressed as a percent coefficient of variation (%CV) was less than 35% for all dose groups.

Individual AUC(tf) instead of AUC(l) values were used in the primary assessment of linearity of desloratadine since in 2 subjects the extrapolated area was >25% AUC(tf).

Figure 3:
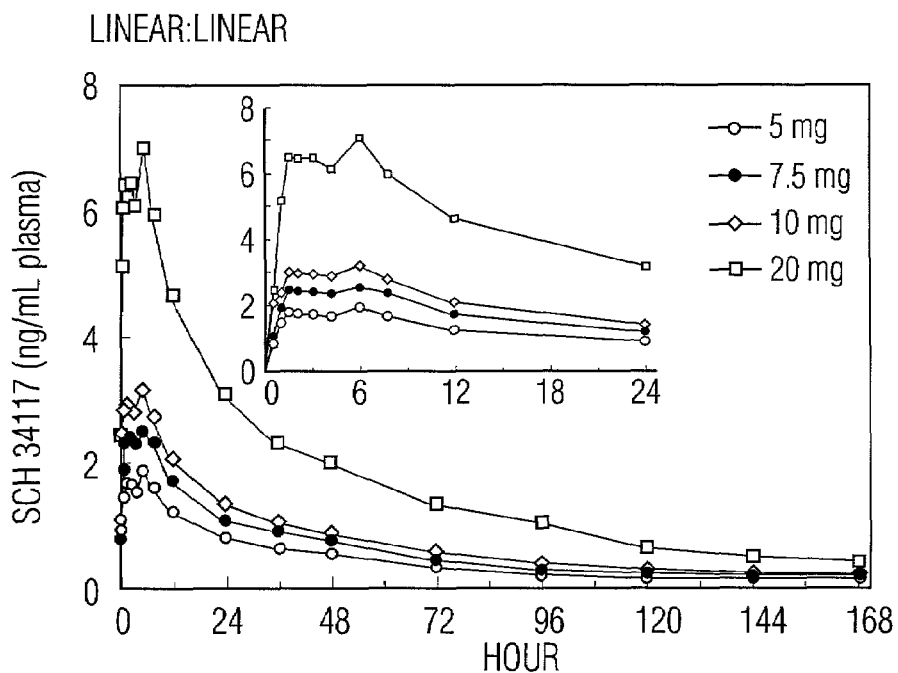
FIG. 3 is a linear: linear graphic display of the mean plasma concentrations of desloratadine ("DL") and 3-OH desloratadine ("3-OH DL") (ng/mL plasma) versus time(0-24 hours), following single-dose oral administration of 5, 7.5,10 or 20 mg desloratadine tablets to healthy adult subjects.
Figure 4:
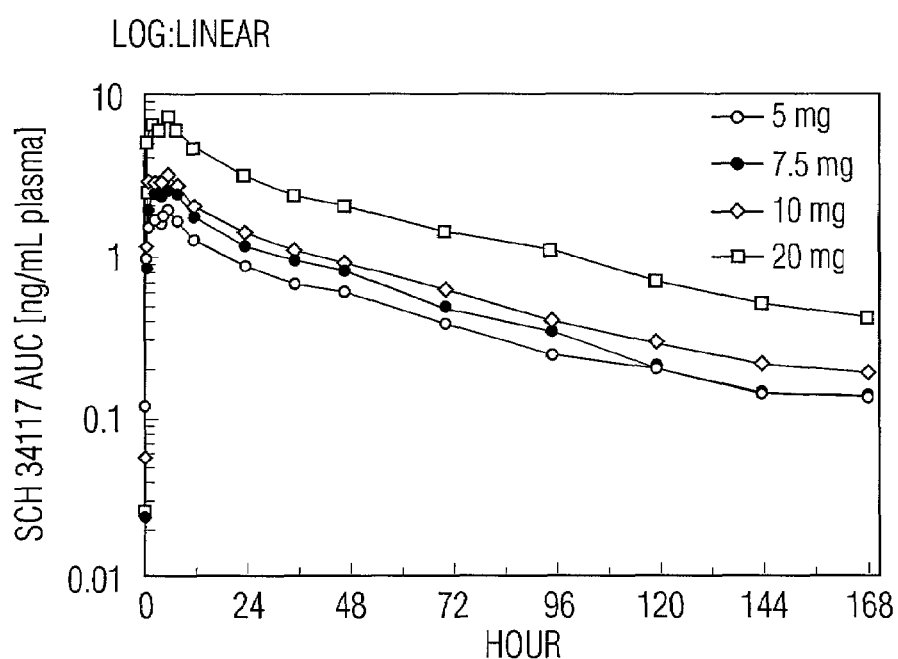
FIG. 4 is a log: linear graphic display of the mean plasma concentrations of desloratadine ("DL") and 3-OH desloratadine ("3-OH DL") (ng/mL plasma) versus time (0-168 hours), following single-dose oral administration of 5, 7.5,10 or 20 mg desloratadine tablets to healthy adult subjects.
Figure 5:
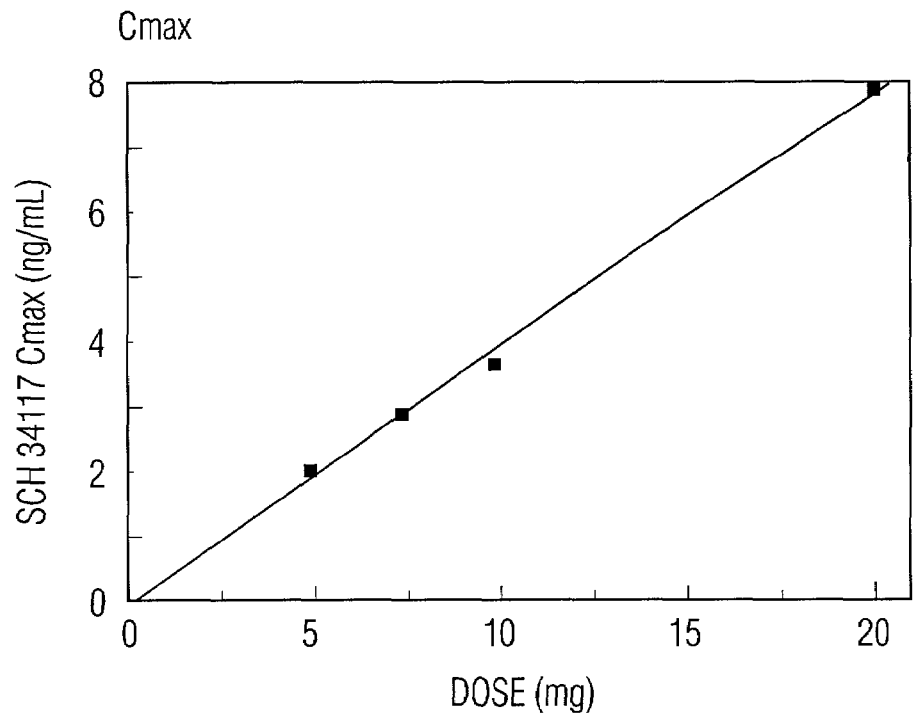
FIG. 5 is a linear: linear graphic display of the linear relationship between the geometric maximum plasma concentrations of desloratadine (ng/mL plasma) and dose, following single-dose oral administration of 5, 7.5,10 or 20 mg desloratadine tablets to healthy adult subjects.
Figure 6:
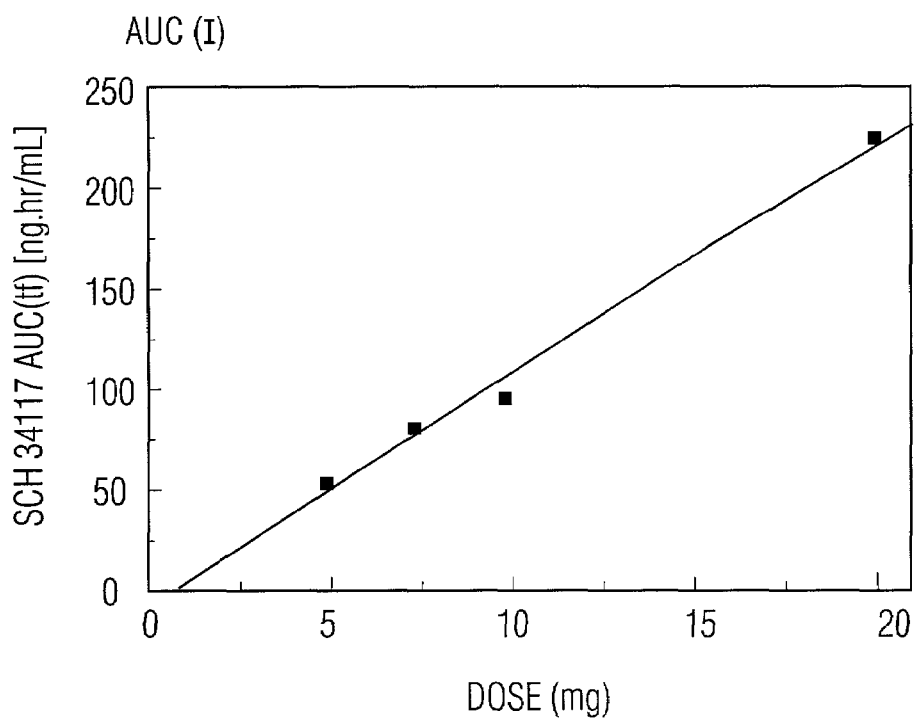
FIG. 6 is a linear: linear graphic display of the linear relationship between the geometric mean area under the plasma concentration of desloratadine vs. time curve (0-24 hours) (ng.hr/mL plasma) and dose, following single-dose oral administration of 5, 7.5,10 or 20 mg desloratadine tablets to healthy adult subjects

FIGS. 3 and 4 show the linear: linear and log; linear relationship between mean plasma desloratadine and time after single oral administration of doses of 5,7.5, 10 and 20 mg of desloratadine to healthy adult male subjects. FIGS. 5 and 6 show the relationship between the geometric means of the pharmacokinetic parameters ($C_{max}$ and AUC) and dose. Linear regression analysis of log dose and log transformed $AUC_{(tf)}$ and $C_{max}$ showed that none of the slopes were statistically significantly different from 1 and the power to detect a 20% difference in slope was >92%. The result of an analysis of variance of the log-transformed dose adjusted (to 1 mg) $C_{max}$ and AUC data from all subjects showed no statistically significant difference for the PK parameters over the dose range 5 mg to 20 mg, support dose proportionality and linear pharmacokinetics.

Discussion and Overall Conclusions

The relationship between dose and the pharmacokinetic behavior of drug is of major interest in drug development. When the processes controlling drug disposition are independent of drug concentration, then all concentration-time curves, when normalized for dose, are superimposable. By using regression analysis and analysis of variance, which makes no assumption about the relationship between the pharmacokinetic parameters and does, it is demonstrated that desloratadine exhibits linear pharmacokinetics over the dose range 5 mg to 20 mg. This shows predictability and linearity in the pharmacokinetics of desloratadine, i.e., a doubling of the dose results in a doubling of concentrations (dose proportionality).

Conclusions

Single oral doses of desloratadine of 5 mg, 7.5 mg, 10 mg and 20 mg administered to healthy male volunteers were safe and well tolerated.

Cmax and $AUC_{(tf)}$ values increased in a dose-proportional manner over the dose range of 5 mg to 20 mg of desloratadine.

Desloratadine has a predictable, linear pharmacokinetic profile.

U.S. Pat. No. 4,659,716 discloses methods of making desloratadine, pharmaceutical compositions containing it and methods of using desloratadine and pharmaceutical compositions containing it to treat allergic reaction in mammals.

U.S. Pat. No. 5,595,997 discloses pharmaceutical compositions containing desloratadine and methods of using desloratadine for treating and preventing various disease states, e.g., allergic rhinitis.

U.S. Pat. No. 4,804,666 discloses 3-OH desloratadine pharmaceutical compositions containing desloratadine and methods of using the allergy in a mammal.

Desloratadine, 3-OH desloratadine and 3-OH desloratadine glucuronide are available from Schering Corporation, Kenilworth, N.J.

The pharmaceutical compositions of desloratadine can be adapted for any mode of administration e.g., for oral, parenteral, e.g., subcutaneous ('SC"), intramuscular ("IM"), and intraperitoneal ("IP"), topical or vaginal administration or by inhalation (orally or intranasally). Preferably desloratadine is administered orally.

Such pharmaceutical compositions may be formulated by combining desloratadine or an equivalent amount of a pharmaceutically acceptable salt thereof with a suitable, inert, pharmaceutically acceptable carrier or diluent that may be either solid or liquid. Desloratadine may be converted into the pharmaceutically acceptable acid addition salts by admixing it with an equivalent amount of a pharmaceutically acceptable acid. Typically suitable pharmaceutically aceptable acids include the mineral acids, e.g., $HNO_3$, $H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salts are trifluoroacetate, tosylate, mesylate, and chloride. Desloratadine is more stable as the free base than as an acid addition salt and the use of the desloratadine free base in pharmaceutical compositions of the present invention is more preferred.

Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa. The preferred tablet formulations are made in accordance with the procedures of U.S. Pat. No. 6,100,274.

Liquid form preparations include solutions, suspensions and emulsions. As an example may be mentioned water or water-propylene glycol solutions for parenteral injection. Solid form preparations may be converted into liquid preparations shortly before use for either oral or administration. Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

Further, desloratadine may be administered as a syrup, tablet, rapidly disintegrating tablet or reditab e.g., such as one that disintegrates in the mouth within seconds of placement on the tongue, or as an extended release formulation of desloratadine in association with therapeutically effective amounts (12 or 24 hour)of an upper airway passage decongestant including, but not limited to phenylephedrine and pseudoephedrine phenylpropanolamine or pharmaceutically acceptable salts thereof, in accordance with the dosing levels known to those skilled in the art and as described in the Physicians' Desk Reference. The use of pseudoephedrine HCl or pseudoephedrine sulfate is preferred.

The present invention provides methods and pharmaceutical compositions that are useful for treatment of allergic and/or inflammatory conditions of the skin (e.g. urticaria) and the upper and lower airway passages including the nasal and non-nasal symptoms of seasonal allergic rhinitis including nasal congestion in a patient in need of such treating. The precise dosage and dosage regimen may be varied by the attending clinician in view of the teachings herein depending upon the requirements of the patient, e.g., the patient's weight and the severity of the allergic and/or inflammatory condition being treated. Determination of the proper dosage and dosage regimen for a particular patient will be within the skill of the attending clinician. The preferred amount of desloratadine which may be delivered by any appropiate pharmaceutical composition is about 5 mg/day or 2.5 mg/twice a day. In accordance with the present invention, about 5.0 mg of desloratadine is administered once a day for about 10 days to a human of 12 years and older having, for example, the nasal and non-nasal symptoms of seasonal and perennial allergic rhinitis and/or the symptoms of chronic idiopathic urticaria, an arithmetic mean steady state maximum plasma concentration ($C_{max}$) of desloratadine is produced in the range about 3.2 ng/ml to about 5.0 ng/ml, preferably about 4 ng/mL, at an arithmetic mean time(or mean time) to maximum plasma concentration ($T_{max}$) in the range of about 2.54 to about 3.96, preferably about 3.2 hours post dose and an area under the concentration-time curve in the range of about 45.5 ng.hr/mL to about 71.1 ng.hr/mL, preferably about 56.9 ng.hr/mL of desloratadine; the geometic mean steady state maximum plasma concentration ($C_{max}$) of desloratadine produced is in the range about 2.90 ng/ml to about 4.54 ng/ml, preferably about 3.63 ng/mL, at an geometic mean time (or median time) to maximum plasma concentration ($T_{max}$) in the range of about 1.60 to about 2.50, preferably about 2.00 hours post dose and the area under the concentration-time curve is in the range of about 39.5 ng.hr/mL to about 61.8 ng.hr/mL, preferably about 49.4 ng.hr/mL of desloratadine. In accordance with the present invention, when about 5.0 mg of desloratadine is administered once a day for about 10 days to said human of 12 years and older, the arithmetic mean steady state maximum plasma concentration ($C_{max}$) of 3-OH-desloratadine produced is in the range of about 1.60 ng/mL to about 2.50 ng/mL, preferably about 2.00 ng/mL, at arithmetic mean time(or mean time) to maximum plasma concentration ($T_{max}$) in the range of about 3.80 to about 5.95 hours post dose, preferably about 4.76 hours post dose, was about, and the area under the concentration-time curve of desloratadineis in the range of about 25.8 ng.hr/mL to about 40.4, preferably about 32.3 ng.hr/mL; the geometic mean steady state maximum plasma concentration($C_{max}$) of 3-OH-desloratadine produced is in the range of about 1.50 ng/mL to about 2.34 ng/mL, preferably about 1.87 ng/mL, at geometic mean time(or median time) to maximum plasma concentration ($T_{max}$) in the range of about 4.00 to about 6.25 hours post dose, preferably about 5.00 hours post dose, was about, and the area under the concentration-time curve of desloratadineis in the range of about 24.3 ng.hr/mL to about 38.0, preferably about 30.4 ng.hr/mL.

While we have hereinabove presented a number of preferred embodiments of this invention by way of example, it is apparent that the scope of the invention is to be defined by the scope of the appended claims.

What is claimed:

1. A method of administering a pharmaceutical composition, wherein the method comprises:
   administering the pharmaceutical composition, comprising desloratadine and a suitable, inert pharmaceutically acceptable carrier or diluent, to target a pharmacokinetic (pK) profile for desloratadine comprising an arithmetic or geometric mean steady state maximum plasma concentration ($C_{max}$) of desloratadine of about 4 ng/mL, and an arithmetic or geometric mean time to maximum plasma concentration ($T_{max}$) of desloratadine of about 3 hours post dose.

2. The method of claim 1, wherein the pharmaceutical composition comprises about 5.0 mg of desloratadine.

3. The method of claim 2, wherein the pharmaceutical composition is administered once a day.

4. The method of claim 1 wherein the desloratadine is in a free base form.

5. A method of administering a pharmaceutical composition, comprising:
   administering the pharmaceutical composition, comprising desloratadine and a suitable, inert pharmaceutically acceptable carrier or diluent, once a day for about 10 days, wherein said administering is carried out to target a pharmacokinetic (pK) profile comprising an arithmetic or geometric mean steady state maximum plasma concentration ($C_{max}$) of desloratadine of about 4 ng/mL, and an arithmetic or geometric mean time to maximum plasma concentration ($T_{max}$) of desloratadine of about 3 hours post dose.

6. The method of claim 5, wherein the pharmaceutical composition comprises about 5.0 mg of desloratadine.

7. The method of claim 5, wherein the desloratadine is in a free base form.

8. A method of administering a pharmaceutical composition comprising:
   administering the pharmaceutical composition, comprising desloratadine and a suitable, inert pharmaceutically acceptable carrier or diluent, for a period of time to target the establishment of a steady-state pharmacokinetic (pK) profile in the bloodstream of a patient comprising an arithmetic or geometric mean steady state maximum plasma concentration ($C_{max}$) of desloratadine of about 4 ng/mL, and an arithmetic or geometric mean time to maximum plasma concentration ($T_{max}$) of desloratadine of about 3 hours post dose.

9. The method of claim 8, wherein the pharmaceutical composition comprises about 5.0 mg of desloratadine.

10. The method of claim 8, wherein the desloratadine is in a free base form.

11. A method of achieving a pharmacokinetic (pK) profile of desloratadine that is safe and effective for treating nasal and non-nasal symptoms of seasonal and perennial allergic rhinitis and for treating symptoms of chronic idiopathic urticaria in a human 12 years or older, comprising:
    administering a dosage form comprising desloratadine and a suitable, inert pharmaceutically acceptable carrier or diluent, wherein said administering is carried out to target the pK profile and wherein the pK profile comprises an arithmetic or geometric mean steady state maximum plasma concentration ($C_{max}$) of desloratadine of about 4 ng/mL, and an arithmetic or geometric mean time to maximum plasma concentration ($T_{max}$) of desloratadine of about 3 hours post dose.

12. A method of treating nasal and non-nasal symptoms of seasonal and perennial allergic rhinitis in a human of 12 years and older comprising:
    administering a dosage form comprising desloratadine and a suitable, inert pharmaceutically acceptable carrier or diluent, wherein said administering is carried out to target a pharmacokinetic (pK) profile that is safe and effective for treating the allergic rhinitis symptoms, and wherein the pK profile comprises an arithmetic or geometric mean steady state maximum plasma concentration ($C_{max}$) of desloratadine of about 4 ng/mL, and an arithmetic or geometric mean time to maximum plasma concentration ($T_{max}$) of desloratadine of about 3 hours post dose.

13. A method of treating symptoms of chronic idiopathic urticaria in a human of 12 years and older comprising:
    administering a dosage form comprising desloratadine and a suitable, inert pharmaceutically acceptable carrier or diluent, wherein said administering is carried out to target a pharmacokinetic (pK) profile that is safe and effective for treating the chronic idiopathic urticaria symptoms, and wherein the pK profile comprises an arithmetic or geometric mean steady state maximum plasma concentration ($C_{max}$) of desloratadine of about 4 ng/mL, and an arithmetic or geometric mean time to maximum plasma concentration ($T_{max}$) of desloratadine of about 3 hours post dose.

14. The method of any of claims 11, 12 or 13, wherein said administering is carried out according to a dosage regimen comprising administering the dosage form once a day for about 10 days.

15. The method of any of claims 11, 12 or 13, wherein said dosage form comprises about 5.0 mg of desloratadine.

16. The method of any of claims 11, 12 or 13, wherein the desloratadine is in a free base form.

* * * * *